United States Patent
Devery et al.

(10) Patent No.: US 8,651,120 B2
(45) Date of Patent: Feb. 18, 2014

(54) TREATMENT DEVICE

(75) Inventors: Cormac John Devery, Felbridge (GB); Thomas Bickford Holbeche, Church Crookham (GB); Geoffrey Morgan Lloyd, College Town (GB)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 13/510,024

(22) PCT Filed: Nov. 11, 2010

(86) PCT No.: PCT/GB2010/002080
§ 371 (c)(1),
(2), (4) Date: Jul. 18, 2012

(87) PCT Pub. No.: WO2011/061477
PCT Pub. Date: May 26, 2011

(65) Prior Publication Data
US 2012/0276499 A1 Nov. 1, 2012

(30) Foreign Application Priority Data
Nov. 17, 2009 (GB) ................................. 0920112.0

(51) Int. Cl.
*A61C 15/00* (2006.01)

(52) U.S. Cl.
USPC ................................. 132/322; 433/88; 601/15

(58) Field of Classification Search
USPC ................ 132/322, 308–311; 433/80–82, 88; 601/15, 16, 18, 21
See application file for complete search history.

(56) References Cited

U.S. PATENT DOCUMENTS

| 4,820,152 A | * | 4/1989 | Warrin et al. | 433/86 |
| 5,123,841 A | * | 6/1992 | Millner | 433/125 |
| 6,135,126 A | * | 10/2000 | Joshi | 132/308 |

* cited by examiner

*Primary Examiner* — Rachel Steitz
(74) *Attorney, Agent, or Firm* — David A. Hey

(57) ABSTRACT

An interdental treatment device comprises a generator 16 for generating a non-thermal gaseous plasma at a temperature suitable for use in oral treatment and an applicator 18 of the non-thermal plasma. The applicator 18 may comprise a hollow needle member for directing a jet of the non-thermal plasma interdentally. Alternatively the applicator 18 may comprise an interdental brush having a hollow head for receiving a non-thermal gaseous plasma, the head having at least one lateral opening for the discharge of the plasma. The generator 16 and applicator 18 may both form part of a hand-held device 10 having its own gas supply in the form of a capsule 12 containing pressurized gas and its own power supply in the form of a battery 20.

6 Claims, 10 Drawing Sheets

TREATMENT DEVICE

FIELD OF INVENTION

The present invention relates to a device for the treatment of teeth.

BACKGROUND OF INVENTION

It is now recognised by dentists that effective interdental cleaning of teeth is crucial to achieving a high level or oral hygiene and in combating oral disease such as gingivitis and periodontis. Dentists therefore recommend to their patients that they regularly floss their teeth. Many patients, however, find it difficult or uncomfortable to floss effectively. The main alternative to flossing is to use an interdental tooth brush. An interdental toothbrush is one which can be inserted in a space between any pair of adjacent teeth in the user's mouth. Various configurations of tooth brush head and bristles are known so as to facilitate interdental cleaning with a toothbrush. In general, however, interdental tooth brushes are not particularly effective and are recognised as inferior to the use of dental floss.

There is therefore a need for improved devices for the interdental cleaning of teeth.

SUMMARY OF THE INVENTION

According to the present invention there is provided an interdental treatment device or tool comprising a generator for creating a non-thermal gaseous plasma at a temperature suitable for use in oral treatment, and an applicator of the non-thermal gaseous plasma, wherein the applicator comprises (i) a hollow, needle member for directing a jet of the non-thermal plasma interdentally, the needle member having at least one inlet port and at least one outlet port or (ii) an interdental brush having a hollow head for receiving the non-thermal gaseous plasma, the head having at least one lateral opening for the discharge of the non-thermal gaseous plasma.

The needle member is preferably detachably engageable with a handpiece having an internal passage for the flow of the non-thermal gaseous plasma.

The term 'non thermal gaseous plasma' includes within its scope a non-thermal gaseous plasma that has partially or totally decayed or collapsed but still contains active species in the form of radicals or excited atoms or molecules. The excited atoms are able to react with ambient air to form single oxygen atoms and hydroxyl radicals.

The term "needle member" is used herein to indicate that the aspect ratio of the member is comparable to that of a needle.

There are two kinds of applicator for use in the device according to the invention. In the first kind, the applicator takes in the form of a needle member. The needle member is not intended for insertion between the teeth; it is instead intended to be held a short distance away from the teeth and is adapted to eject a high velocity flow of non-thermal gaseous plasma. The needle member can be pointed at each interdental space to be treated in turn, so that on activation of the device a jet of non-thermal gaseous plasma is ejected at these spaces. Some of the non-thermal gaseous plasma penetrates the interdental spaces and has a cleaning effect.

In an assembled device according to the invention the needle device has an outlet port that directs gas at an angle of 90° to 160° to the longitudinal axis of a handpiece which receives the needle member.

The needle member is preferably curvilinear or has an elbow. It may, for example, be claw-shaped or talon-shaped.

The said inlet port is preferably a single axial opening at the proximal end of the needle member.

The said outlet port is preferably a single axial part of the distal end of the needle member. This outlet port preferably has a diameter of less than 2 mm, more preferably less than 1 mm. By employing such a small diameter outlet, the creation of an exit gas velocity which is effective to penetrate interdental spaces is facilitated. Typically, the exit velocity is in the range 20-100 ms$^{-1}$. Alternatively, the distal end of the needle member may be closed and one or more outlet ports may be formed through the needle at an angle to its axis.

The needle member may be formed of any convenient material, for example, a plastics material, an elastomeric material, or an alloy such as stainless steel.

The applicator may alternatively take the form of an interdental brush. The head of the brush may comprise a hollow wire with an array of bristles extending outwards from it. At least some of the bristles may be hollow and open at their ends so as to permit interdental ejection of the non-thermal gaseous plasma. Alternatively, or in addition, the wire itself may at its head be perforate or have gas outlet orifices formed therein.

If the device according to the invention is to be used in a dental surgery, a supply of gas under pressure for the formation of the plasma, an electrical power source, an electric signal generator for converting the electrical power into a series of electrical voltage "pulses" suitable for generating the plasma, and the plasma generator itself may all be external to so the handpiece.

Alternatively, however, the handpiece may house the plasma generator and preferably a gas capsule for storing a gas under pressure and supplying a flow of gas to the plasma generator when released from the capsule; a source of electrical energy; energising means electrically connected to the source of electrical energy for energising gas in the plasma generator to form said non-thermal gaseous plasma, wherein the device has a size and weight such that the device can be held and operated by a user by hand. In an alternative embodiment, the capsule may be engageable with the handpiece from outside the handpiece. In a further embodiment, the plasma generator, the source of electrical energy and the energising means are all located in a separate housing which engages the capsule from outside, the capsule itself typically forming the handpiece.

The non-thermal plasma may be generated at a temperature less than 40° C.

A control may be provided for selectively releasing gas from the gas capsule for forming said flow of gas. Said control may additionally be operably connected to said energising means for controlling energisation of the electrodes. A sensor may be provided for sensing the flow of gas released from the gas capsule and wherein said control allows activation of the energising means only if said flow of gas is above a predetermined mass or volume flow rate or has been established for a predetermined period of time. The control may comprise a user input means, such as a manually operable button or switch, operable by a user for causing flow of gas to said reaction generator and activation of the energising means.

The handpiece may house means for locating a said gas capsule in or on said handpiece so that the gas capsule is operable to release gas for forming said gas flow and wherein said locating means is adapted such that a said gas capsule can be removed from the handpiece so that a replacement said gas capsule can be located in said handpiece by said locating means. A gas release mechanism may be operable for releasing gas from the gas capsule when said locating means locates a said gas capsule in said handpiece. The gas capsule may comprise a pressure release valve, such as Schrader valve, biased to prevent the release of gas from the gas capsule and said gas release mechanism comprises means for operating on said pressure release valve against said bias for releasing gas from the gas capsule.

The handpiece may comprise a conduit extending between the gas capsule and the plasma generator for directing the flow of gas released from said gas capsule to the gas capsule. A flow valve which when open may allow said flow of gas through the conduit from the gas capsule to the plasma generator, and when closed may resist said flow. Alternatively or additionally, a flow regulator may be provided for regulating the flow of gas between the gas capsule and the plasma generator and/or the flow of species from the plasma generator to the applicator. In this way, the flow of gas entering the plasma chamber can be controlled to allow plasma to occur and the flow of species ejected from the device can be controlled to allow treatment to occur.

An expansion chamber may be provided immediate the gas capsule and the plasma generator in which gas can be released from the gas capsule for controlled release through an orifice plate. The expansion chamber reduces flow speed from the gas capsule.

The gas capsule contains a sufficient amount of gas prior to use for generating a plasma species for a time sufficient to achieve a beneficial interdental clawing effect. In this regard, the gas capsule preferably contains a sufficient amount of gas for generating a plasma for at least two minutes. The generation of species sufficient to provide a beneficial interdental clawing effect region (such as the teeth in an oral cavity) may require generally half a liter of gas per minute at atmospheric pressure. Accordingly, the gas capsule may contain the equivalent of up to four liters of gas at atmospheric pressure stored at a pressure of at least 60 bar. The internal volume (water capacity) of the gas capsule may be in the range of 10 ml to 100 ml. The gas capsule may be generally cylindrical and less than approximately 100 mm in length and 35 mm in diameter.

The energising means may comprise at least one electrode for generating an electric field in said plasma generator and a signal generator for generating an electrical signal for driving said at least one electrode. The energising means may be configured to generate a non-thermal plasma at a temperature which is preferably in the range from 10° C. to 40° C. which is tolerable by a user. At least one of said electrodes may be insulated from gas in the plasma generator by a dielectric to reduce arcing and thereby limit heating of the species. Where two or more electrodes are employed they may be spaced apart one from another in order to generate an electric field in substantially all of the plasma generator. One of the electrodes may be formed around a periphery of the plasma generator. One of the electrodes may be formed by a probe extending into the plasma generator. The probe may be tapered at an end portion thereof to form a point for increasing the generation of plasma in said plasma generator.

Said signal generator may be configured to generate an AC signal, a pulsed DC signal or an RF signal for driving said electrodes which may be at a low duty cycle signal in which the energy is provided to the or each of the electrodes for less than 25% of the cycle. Typically the energy is provided for 10 to 20% of the cycle.

Said energising means may comprise an amplifier for amplifying the signal for driving the electrodes and a matching circuit for matching impedance of the load and the source.

The source of electrical energy may be one or more disposable or rechargeable batteries. The batteries are preferably rechargeable and said housing comprises a socket for receiving a plug connected to a mains power source and a recharging circuit for recharging the batteries. Alternatively, the device may comprise means for inductively coupling the batteries to a recharging unit for recharging. The housing may comprise an enclosure for locating the batteries in the housing and electrical terminals which connect to the batteries when located in said enclosure for supplying energy to said energising means.

Alternatively, the source of electrical energy may comprise a transformer and said housing comprises means for connected to an electrical power supply and wherein said transformer is adapted to supply energy to said energising means.

A display may be provided for displaying a value representative of a condition of said device which may be one or more of: the gas content of the capsule, the amount of charge remaining in the source of electrical energy, or a temperature of the plasma emitted from the device. Means may be provided for alerting a user, such as a sound which is audible to user or a warning light, when a condition of said device decreases below a predetermined amount.

The gas capsule may contain a gas having low energy requirement for forming a plasma in said reaction chamber. In this way, the amount of energy injected into the reaction chamber can be reduced thereby avoiding excessive heating of the gas or species. The gas may be a noble gas such as helium or argon. Although such noble gases are normally non-reactive, when in plasma form, they can, we believe, reduce into the plasma set and react with oxygen molecules and water vapour molecules in the human mouth to form respectively oxygen and hydroxyl free radicals which are effective anti-bacterial spaces and therefore contribute to the interdental cleaning of teeth.

In order to permit the device to be used by hand, it is preferable that it is less than 300 mm in length and 50 mm in breadth and has a mass of less than 1 kg.

The present invention also provides apparatus comprising the device and a recharging unit comprising: a recharging gas pressure vessel containing gas for supplying gas to the gas capsule of the device; and/or electrical recharging means for recharging said source of electrical energy in said device.

The recharging unit and gas capsule of the device may comprise respective recharging valves which can be opened when the device and unit are connected to allow the supply of gas to the gas capsule and are closed when not connected.

The recharging unit may comprise a seat for seating the device, and wherein when the device is seated in the recharging unit the gas capsule and the recharging pressure vessel are connected to allow the supply of gas to the gas capsule. A conduit may be provided having a first end portion adapted for engaging with and opening the recharging valve of the gas capsule and a second end portion for engaging with and opening a recharging valve of the device pressure vessel. Alternatively, the recharging apparatus may comprise a seat for seating the gas capsule when it has been removed from said device and wherein when the gas capsule is seated in the recharging unit the pressure vessels are connected to allow the supply of gas to the gas capsule. In this arrangement, at least two gas capsules may be provided, such that at any one time one capsule can be seated in the recharging unit for recharging and one capsule can be housed in said device housing for use in generating a non-thermal species.

The electrical recharging means may comprise a recharging circuit for receiving electrical energy from a supply and supplying said electrical energy for recharging said source of electrical energy in said device when said source of energy is connected to said electrical recharging means. The recharging unit may comprise a seat for seating the device, and wherein when the device is seated in the recharging unit said source of energy is connected to said electrical recharging means for recharging said source of electrical energy.

Alternatively, the recharging unit may comprise a seat for seating said source of electrical energy when said source has been removed from said device and wherein when said source is seated in the recharging unit said source of energy is connected to said electrical recharging means for recharging said source of electrical energy.

Preferably, the needle member is replaceable by at least one other applicator having a configuration suited to an oral healthcare application other than interdental cleaning. There is preferably activation means in the handpiece for allowing activation of the plasma generator only when the needle member or other applicator engages the handpiece.

One of the applicator and the handpiece may comprise locking protrusions and the other of the applicator and the handpiece may comprise locking recesses for recessing the locking positions and for locking the applicator to the handpiece. In a set of applicators for use in the device, each applicator may have a different configuration of locking recesses or locking protrusions.

In another embodiment of a device according to the invention there is a first needle member which is replaceable by a second one of different configuration from the first. For example, the first needle member may be configured for the interdental treatment of front teeth and the second needle member may be configured for the interdental treatment of back teeth.

The interdental treatment device according to the invention may be sold as a kit with one or more extra applicators. The device need not be fully assembled in the kit.

One of the applicator and the handpiece may comprise locking protrusions and for locking the applicator to the handpiece in a set of applicators for use in the device, each applicator may have a different configuration of locking recesses or locking protrusions.

In another embodiment of a device according to the invention there is a first needle member which is replaceable by a second one of different configuration from the first. For example, the first needle member may be configured for the interdental treatment of front teeth and the second needle member may be configured for the interdental treatment of back teeth.

The interdental treatment device according to the invention may be sold as a kit with one or more extra applicators. The device need not be fully assembled in the kit.

BRIEF DESCRIPTION OF THE DRAWINGS

In order that the present invention may be well understood, embodiments thereof, which are given by way of example only, will now be described with reference to the accompanying drawings, in which.

DETAILED DESCRIPTION OF ILLUSTRATED EMBODIMENTS

Figure 1:
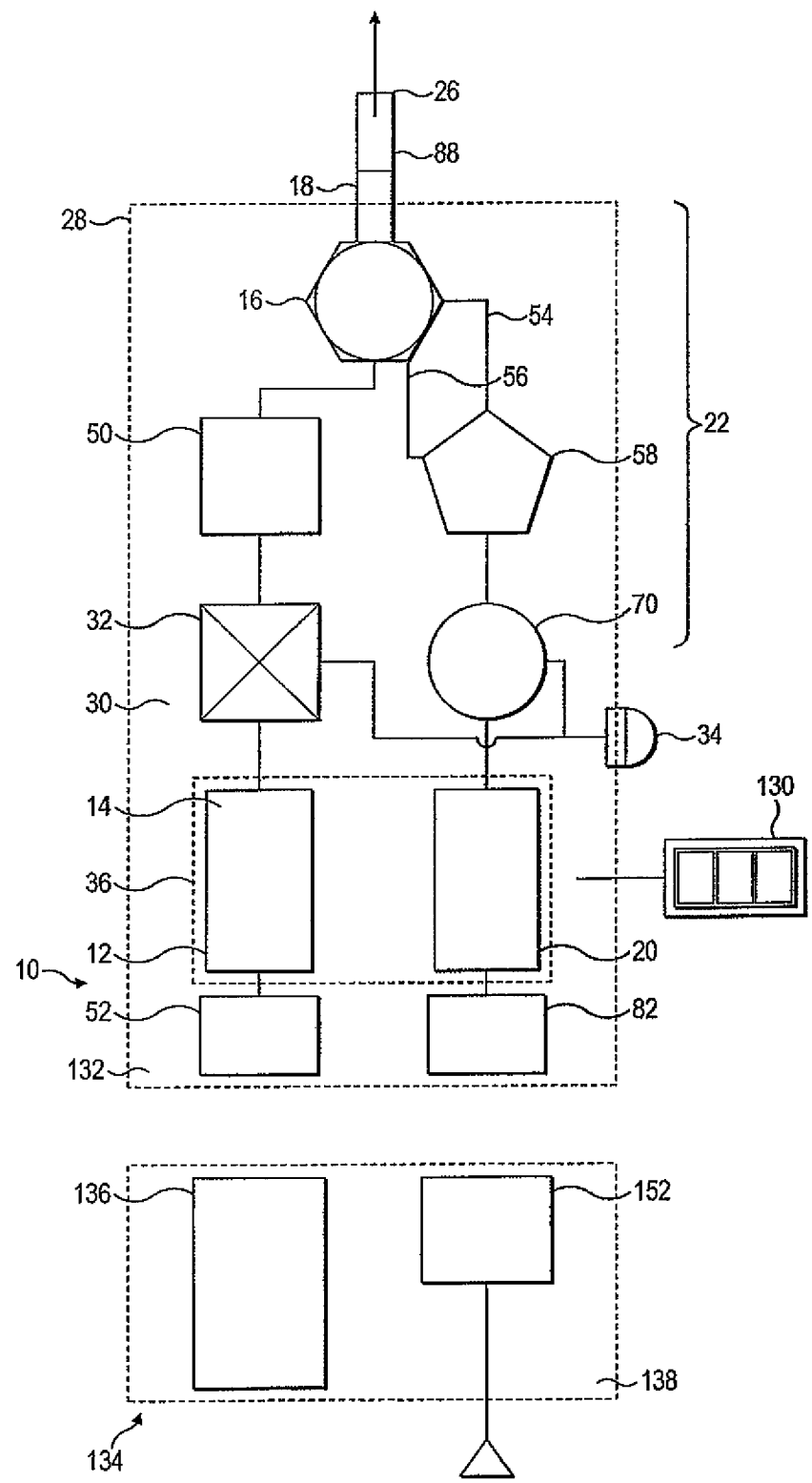
FIG. 1 shows schematically apparatus comprising a device for generating a non-thermal plasma and a recharging unit.
Figure 2:
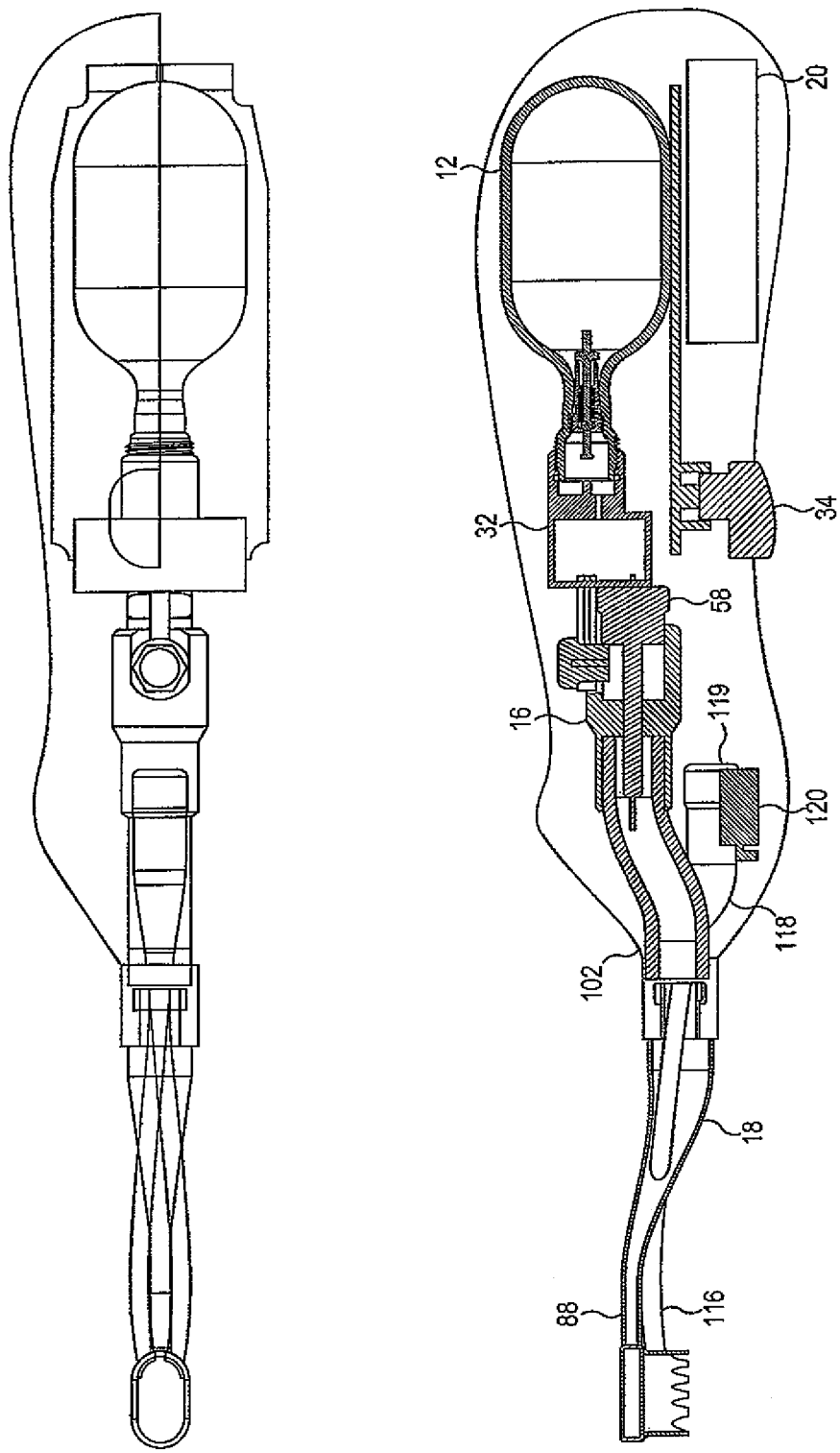
FIG. 2 shows a perspective cut-away view of the device.

Referring to FIGS. 1 and 2, a device 10 is shown for generating a non-thermal plasma 24 which may be a flow of gas plasma in the form of a gas plasma plume or jet emitted from the device. The flow of gas plasma is generated and emitted from the device generally at atmospheric pressure. The device comprises a gas capsule, or pressure vessel, 12 for holding a gas or gases 14 under pressure and forming a flow of gas through a plasma generator 16 to an applicator 18 when released from the capsule. Gas released from the gas capsule is energised in the plasma generator to form a gas plasma.

Figure 1A:
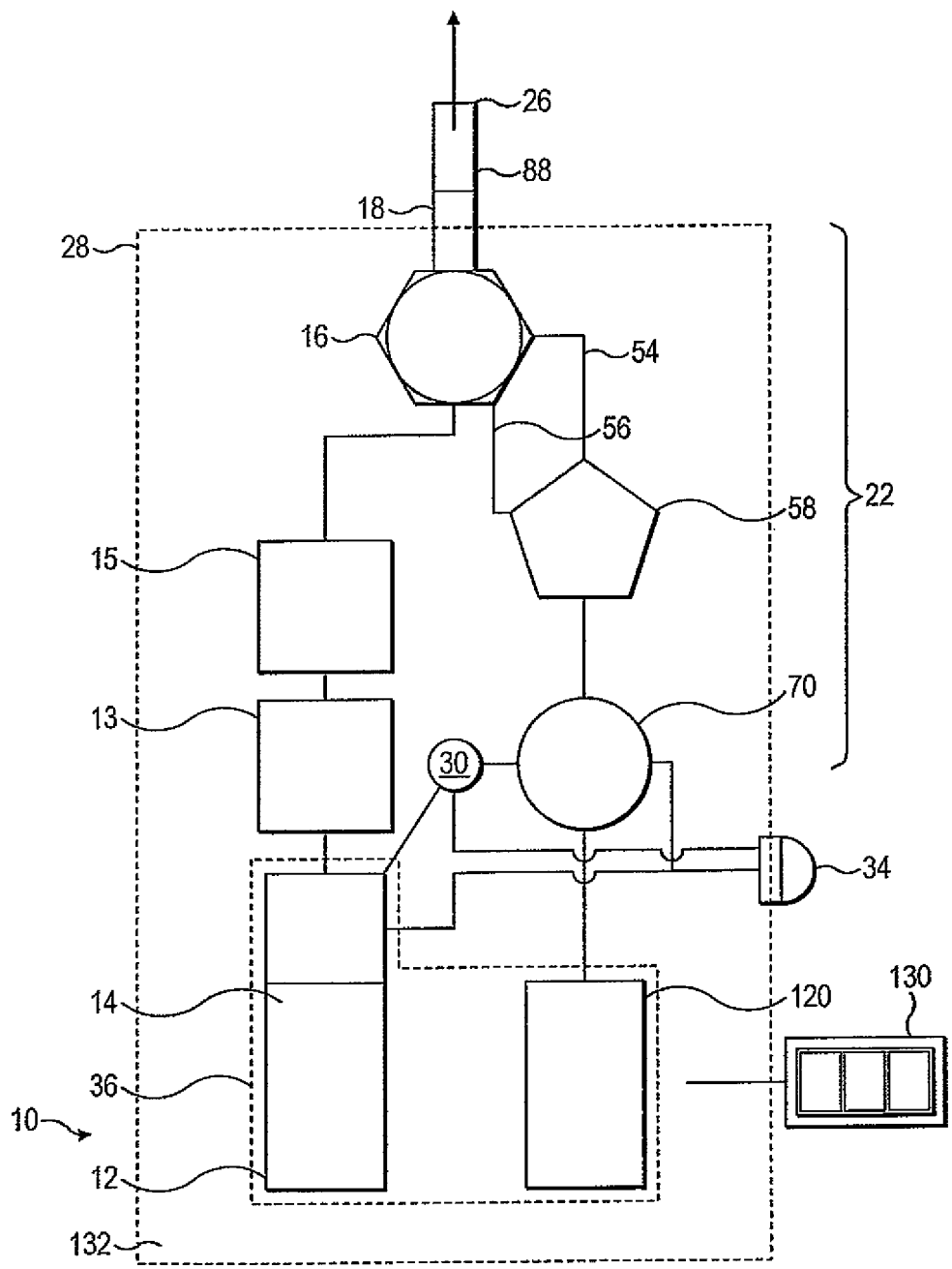
FIG. 1a shows a modified device.

In a modified device shown in FIG. 1a, high pressure gas may flow from the capsule through an orifice plate 13 into an expansion chamber 15 which slows flow and which can then be released in a controlled way to the reaction generator 16.

The device further comprises a source of electrical energy 20 and gas plasma energising means 22 electrically connected to the source of electrical energy for energising gas 14 in the plasma generator 16 to form a gas plasma 24. The applicator 18 directs flow of plasma from the plasma generator 16 for generating a gas plasma plume from an opening 26 in the applicator.

A handpiece 28 houses the gas capsule 12, plasma generator 16, source of electrical energy 20, and plasma energising means 22. The device is sized and of a weight such it can be held and operated by a user by hand and the plasma 24 readily directed by a user to treat a treatment region of an object or human or animal body. In this regard, the device is operable without the requirement for its connection by a gas line to a gas supply. Such a prior art arrangement is cumbersome and does allow the device to be portable. The self-contained arrangement of the device 10 allows easy use in a domestic environment, for instance, in a bathroom. The device 10 may receive power from the source without the requirement for electrical cabling connecting the device to a mains supply. However, typically electrical cabling is less of an impediment to use in the domestic environment than a gas line, as cabling is usually flexible and light-weight, although in device 10 electrical cabling is not required when the device is in use.

In order that the device is suitable to be held and operated by hand, it should not exceed an upper size or an upper weight. It will also be appreciated that treatment of a treatment region using the device may require intricate and fine movements which are possible if the device is hand-held only if it is relatively light. In one example, the device is approximately the size and mass of a typical electric tooth brush. Other known hand-held and operated devices in other fields, which are provided herein to aid understanding of the size and mass of the device 10, are for example a cordless electric drill or screw driver. Accordingly, the upper size of handpiece 28, or the device as a whole, is approximately 30 cm in length by 5 cm in breadth. The upper limit of the breadth is determined by the ability of a hand to hold the device. Any size of housing significantly above 50 mm diameter renders the device uncomfortable to hold and use. The upper of the length is determined by the ability of a user to use the device without it becoming unwieldy and it will also be appreciated that because the device is used to treat teeth, the device will normally be less than an arm's length and preferably in the region of about 20 cm. Preferably, the handpiece 28 is contoured to so that it can be held comfortably in the palm of the hand. The mass of the housing, or device as a whole, is preferably less than one kilogram.

The components of device 10 will now be described in more detail, giving modifications and alternatives where relevant.

A control indicated generally at 30 is provided for selectively releasing gas from the gas capsule for forming the flow of gas. As shown in this example, the control comprises a valve 32 which when open allows the flow of gas through a conduit from the gas capsule to the plasma chamber, and when closed resists flow. The control 30 comprises a mechanical push switch 34 which can be operated by a user for controlling the valve 32. Alternatively, other user activation means can be provided to operate the valve, such as a mechanical slide switch or an electronic switch which can be closed for example to open a solenoid valve. Still further, the user activation means may be adapted such that flow can be activated from the gas capsule in response to first user input and deactivated in response to a second user input. Alternatively, a single user input may activate a timer circuit (not shown) to allow gas flow for a predetermined period of time sufficient to treat a treatment region. For example if the device 10 is used for teeth whitening the predetermined period may be 5 seconds for each tooth.

The valve 32 may be any suitable means for opening and closing flow between the gas capsule and the plasma generator. Further, the valve may be variable for adjusting the flow between fully open and fully closed, for example a butterfly valve.

The handpiece 28 comprises means 36 for locating the gas capsule 12 in the housing so that the gas capsule is operable to release gas for forming the gas flow. The locating means 36 may be adapted such that the gas capsule 12 can be removed from the housing for example when the gas contained therein is depleted or low so that a replacement gas capsule which is full can be located in the housing. In this regard, the locating means may comprise a chamber shaped for receiving the gas capsule and a closure member (not shown) for closing the chamber when the gas capsule is located in the chamber. In another example, the gas capsule may be push-fitted or screw-fitted into the chamber.

The handpiece may comprise a formation or other gas release mechanism operable for releasing gas from the gas capsule when the locating means locates the gas capsule in the chamber. The gas capsule may comprise a pressure release valve biased to prevent the release of gas from the pressure vessel. The gas release mechanism operates on the pressure release valve against the bias for releasing gas from the capsule.

Figure 3:
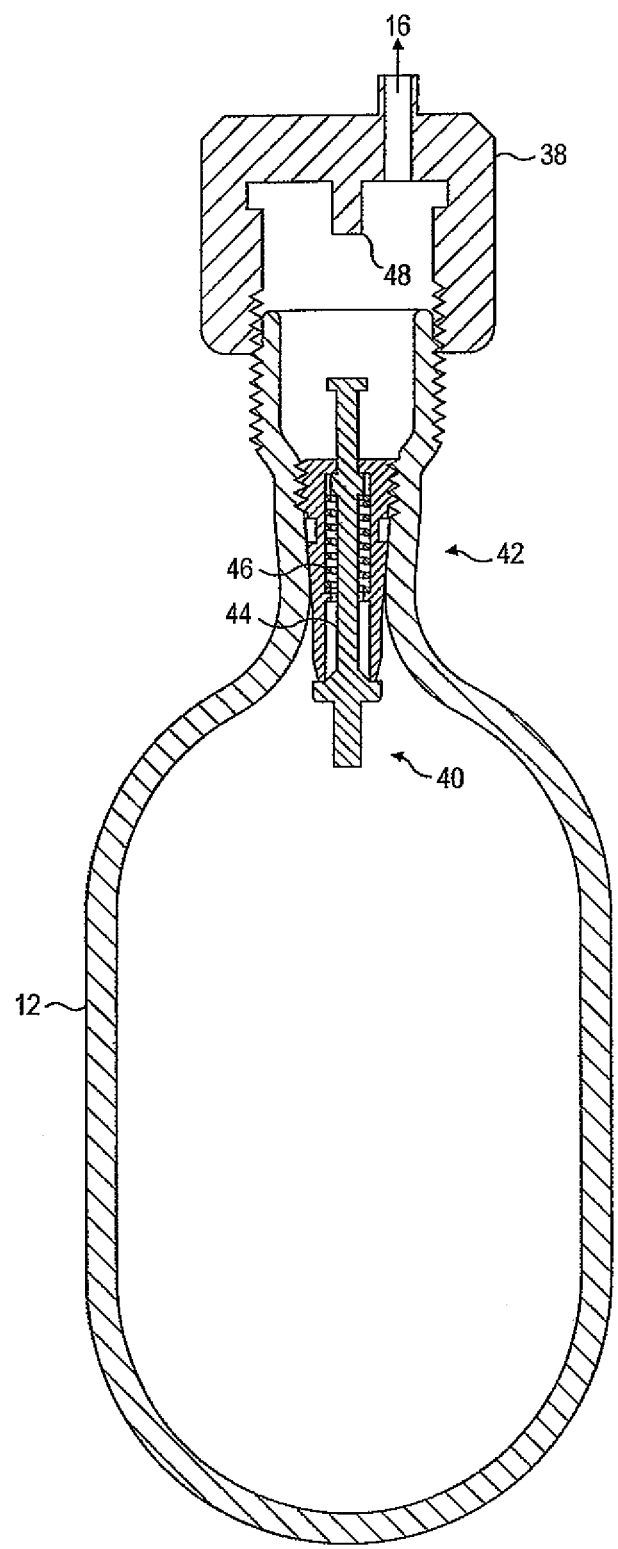
FIG. 3 shows a cut-away view of a pressure vessel of the device.

One example of the gas release mechanism and pressure release valve is shown in FIG. 3. The housing comprises a conduit 38 extending between the gas capsule 12 and the plasma generator 16 for directing the flow of gas released from the gas capsule. The gas capsule 12 comprises a valve 40 at the head 42 of the capsule. In this example locating means comprises an outer surface of the head 42 which is threaded for engaging with a complimentary threaded surface of the housing for locating the pressure vessel in position. The valve 40 comprises a sliding member 44 received for sliding movement in the neck of the pressure vessel and biased by a biasing means, which in this example is a spring 46, into a closed position. When the pressure vessel is located in the housing, a formation, or protrusion, 48 engages the sliding member 44 pushing it into the vessel (as shown by arrows in FIG. 3) and opening the valve to allow gas flow from the vessel. The valve 40 has sufficient sealing strength to retain gas in the pressure vessel at the maximum pressure of the vessel, for example, 80 bar. The valve may be a Schrader valve.

Although a separate valve 32 is shown in FIG. 1 for selectively allowing flow of gas to the plasma generator 16 in addition to the pressure release valve 40, in an alternative arrangement, the valve 32 can be omitted such that control of gas flow is controlled solely by the pressure release valve optionally into an expansion chamber 11 and released in a controlled fashion via an orifice plate.

The mass or volume flow rate of gas entering the plasma chamber 16 may be regulated so as to control the generation of plasma. For instance, the rate of flow controls the residence time of gas in the plasma chamber. Accordingly, the device 10 may comprise a flow regulator 50 for regulating the flow of gas between the gas capsule and the plasma generator. Additionally or alternatively, a flow regulator can be located to regulate the flow of gas and plasma from the plasma generator. The flow regulator may be a variable flow control valve arranged in a feed back loop with a flow sensor 72 (see FIG. 4). As an alternative to a flow regulator, a pressure regulator may be provided for regulating the pressure of gas in the plasma generator. Preferably, the flow regulator is operable to achieve constant flow of gas to the plasma generator throughout a pressure range of gas in the gas capsule that is, relatively high pressure when the capsule is full and relatively low pressure when the capsule becomes empty.

The required amount of exposure of interdental treatment regions to plasma (or other gas species generated by the plasma) varies according to the size of the gaps between the user's teeth. The gas capsule preferably contains a sufficient amount of gas prior to use for generating a plasma.

The gas capsule may contain a sufficient amount of gas for generating a plasma plume or jet for at least two minutes.

The amount of gas which can be contained in the pressure vessel, or gas capsule, is limited by the design of the pressure vessel and overall weight and size of the device. In this latter regard, a relatively heavy pressure vessel may be capable of storing large quantities of gas, however, such a heavy vessel is not suitable for the device 10 as it would render the device incapable of being held and operated by hand. It has been found that a suitable gas capsule is adapted to contain the equivalent of approximately four liters of gas at atmospheric pressure stored at a pressure of at least 80 bar. The gas capsule may have an internal volume sufficient to contain between 10 ml to 100 ml of water. The gas capsule may be generally cylindrical and less than 100 mm in length and 35 mm in diameter. In the example shown in FIG. 2, the gas capsule is approximately 100 mm in length and 35 mm in diameter. The vessel may be made from aluminium or stainless steel, or mild steel or any other suitable robust material.

As shown in FIG. 1 and described in more detail below, the device 10 comprises a filler valve 52 for allowing gas from a gas supply to re-fill or recharge the gas capsule 12. The filler valve 52 is in normal use, closed to prevent evacuation of gas from the gas capsule and can be opened when it is desired to recharge the vessel. The valve 52 may be similar to the arrangement shown in FIG. 3 in that a recharging unit engages with the valve 52 to open the valve and allow the recharging of gas. Additionally, the gas capsule may be formed integrally and form part of the housing 28 and re-filled when empty.

Alternatively the gas capsule 12 can be withdrawn from the device 10 and inserted into the recharging unit 134 by the user.

The plasma energising means 22 comprises two electrodes 54, 56 for generating an electric field in the plasma generator 16. In certain configurations a single electrode may be provided and more than two electrodes may be provided for example with two electrodes receiving a driving signal and one electrode being earthed. A signal generator 58 generates an electrical signal for driving, or energising, the electrodes. At least one, and preferably both or all, of the electrodes are dielectric barrier discharge electrodes insulated from gas in the plasma chamber by a dielectric to prevent excessive heating of the plasma caused by continuous or prolonged arcing. Suitable dielectric materials are ceramic, plastics or glass. Insulating the or each electrode reduces the duration of arcing in the plasma chamber when an electric current flows from one electrode through the plasma or gas to the other electrode or each of the other electrodes.

Figure 4:
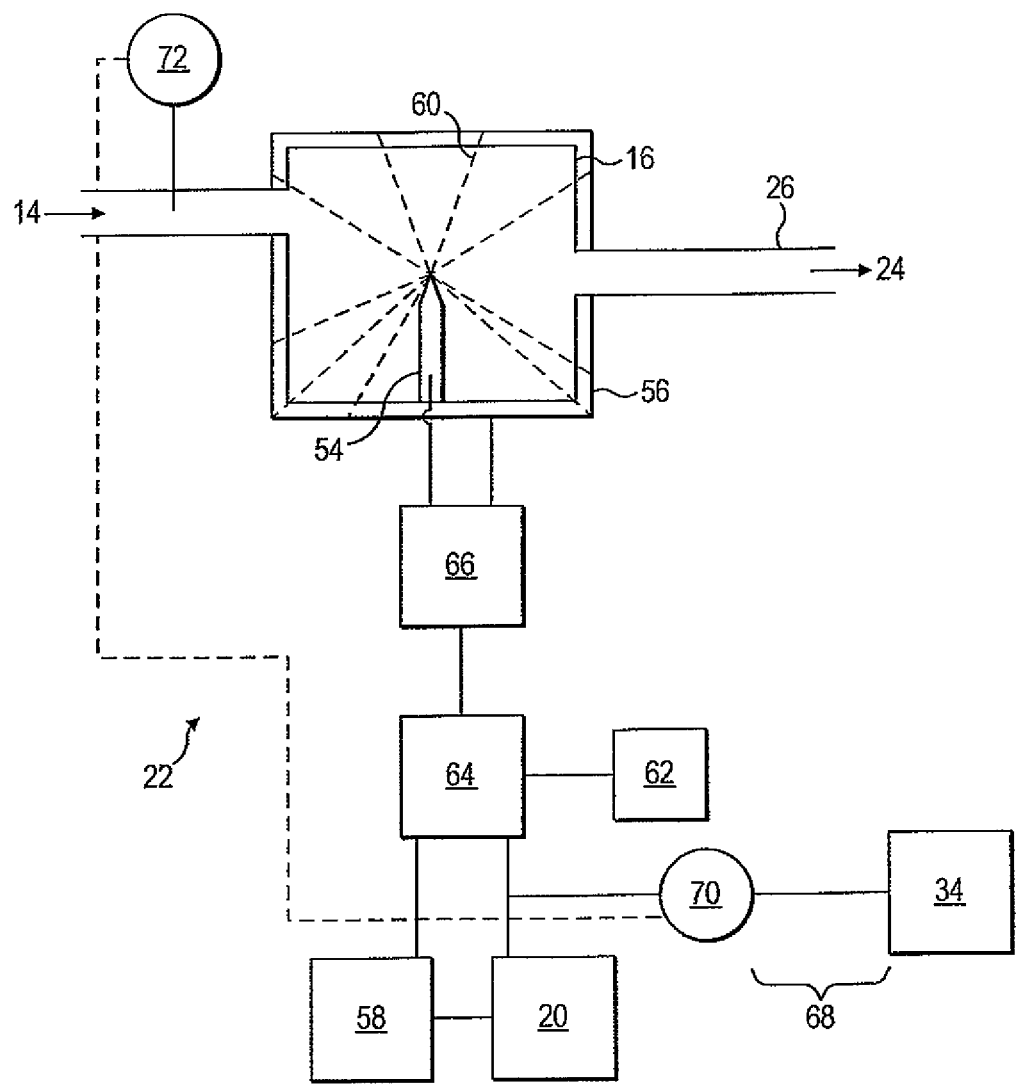
FIG. 4 shows schematically a plasma generator and means for energising gas in the generator.

Referring to FIG. 4, the electrodes 54, 56 are spaced apart one from another in order to generate an electric field shown by field lines 60 in substantially all of the plasma chamber 16. In this way, it is possible to increase the formation of plasma since gas in all portions of the plasma chamber interacts with the electric field.

One of the electrodes 56 is formed around a periphery of the plasma generator If the plasma generator is formed from a dielectric the electrode may be embedded in the structure of the wall of the plasma generator or on the outer surface of the wall. If the plasma generator is formed from an electrical conductor, the wall of the plasma generator itself may act as an electrode.

It has been found that plasma generation is promoted if one of the electrodes 54 is formed by a probe extending into the plasma generator The probe is tapered at an end portion thereof to form a point for increasing the generation of plasma in said plasma generator. In this regard, the density of electric field is increased particularly in the region of the plasma generator proximate the point of the probe. The probe may be electrically insulated along its length with a dielectric.

The plasma energising means may operate so as to provide high voltage pulses. A timing circuit 62 may switch the signal output off and on over the required duty cycle so as to separate the pulses.

In one arrangement, signal generator 58 is configured to generate an AC signal output at 1 kV and 30 to 80 kHz for driving the electrodes 54, 56. This range is greater than 20 kHz so that signal generator is not typically audible to people during use. Use at less than 20 kHz may produce audible hissing.

In the AC example shown, the plasma energising means 22 comprises an amplifier 64 for amplifying the output from the signal generator for driving the electrodes. A suitable matching circuit 66 may be provided for matching impedance of the load and the source.

In an alternative arrangement a pulsed DC signal is generated from a 12V battery. The signal generator may through a number of components and circuits (not individually shown) convert the electrical current from a 12V battery into a pulsed output voltage in the range 4 to 6 kV at a frequency of 2-10 kHz which is suitable for generation of a non-thermal plasma. Such circuits and components are well known in the fields of electronics and electrical engineering and need not be described in full detail herein. Essentially circuits of a kind used with xenon flashlamps can be used to enable the battery to charge a capacitor up to, say, 320V. A transformer can be used to set up the voltage and enable voltage pulses in the desired range of 4 to 6 kV to be generated. In order to produce clear, well defined pulses it is desirable to keep the number of turns and inductance of the windings of the transformer to low levels and to have modest step-up ratios. This approach helps keep the unwanted parasitic elements of leakage inductance and stray winding capacitance to a minimum, both of which contribute to pulse distortion.

Because a pulse transformer has low primary winding inductance, the magnetising current that generates the working magnetic flux in the core is substantial, leading to significant stored magnetic energy in the transformer during the pulse generation. For an efficient design, this magnetic energy is recovered at the end of the pulse and temporarily held in another form (usually as a charge on a capacitor) ready to generate the next pulse.

In any case, the magnetic flux in the core must be returned to zero before the next pulse is generated otherwise the flux builds up with successive pulses until the core saturates, at which point the transformer stops working and acts as a short circuit to the drive electronics.

A common method of magnetic energy recovery in switched-node power supply transformers, which may be used in this case, is through the use of a so-called "flyback" winding. This is usually identical to the primary winding and both wound on the core at the same time (a bipolar winding) in order to ensure a high level of magnetic coupling between the two. The flyback winding connects between ground and the reservoir capacitor of the DC supply via a blocking diode.

During pulse generation a fixed voltage is applied to the primary winding and current ramps up building up magnetic flux in the core—this induces an equal and opposite voltage across the flyback winding (but no current flows due to the blocking diode). Interruption of the primary current at the end of the pulse forces the magnetic field to start collapsing which reverses the induced voltage across the flyback winding and causes current to flow back into the supply capacitor. The flux and current ramp down smoothly to zero ready for the next pulse.

Another suitable transformer configuration is a push-pull design in which two identical bifilar wound primary windings are alternately connected to the DC power supply. The phasing of the windings is such that magnetic flux in the core is generated with opposing directions which each is alternately driven.

A push-pull design also allows stored magnetic energy to be recovered and returned to the supply capacitor in a very similar fashion to the flyback approach, where the blocking diode now becomes an active transistor switch. The same transformer design may be used for either approach.

Although the push-pull design requires additional switching transistor and control, it allows the possibility of doubling the change in magnetic flux within the limits of the core by using both positive and negative flux excursions. The flyback design outlined above only allows unipolar flux excursions.

For a given flux ramp rate, the push-pull design has the capability to produce a continuous pulse with twice the duration of a flyback version using the same transformer. Referring now to FIG. 4, a control 68 is operably connected to the plasma energising means 22 for controlling energisation of the electrodes. In this example the control 68 comprises an electrical switch 70 which when closed allows energisation of the electrodes 54, 56. The switch 70 is manually operable by a user using the previously referenced button switch 34 (which also activates valve 32). Alternatively, a separate user input device may be used to operate switch 70. The use of the same user input device for controlling the flow of gas into the plasma chamber and the energisation of the electrodes 54, 56 is desirable because preferably gas flow and energisation of the electrodes occurs at the same time or there may be a predetermined time delay between gas flow and energisation. Further, it is preferable that energisation of the electrodes does not occur unless gas flow exceeds a predetermined minimum required flow. Accordingly, the control 68 and control 30 may be integrated and comprise flow valve 32 for allowing the flow of gas 14 and switch 70 for allowing energisation of the electrodes.

As shown in FIG. 4, a sensor 72 is provided for sensing the flow of gas 14 released from the pressure vessel 12. The control 68 allows energisation of the electrodes only if the flow of gas is above a predetermined mass or volume flow rate or has been established for a chosen period of time.

Figure 5:
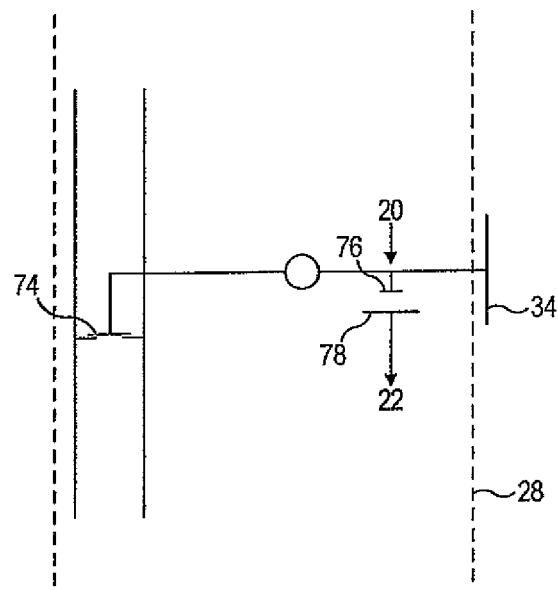
FIGS. 5 and 6 show a simplified mechanical linkage for operating the device.
Figure 6:
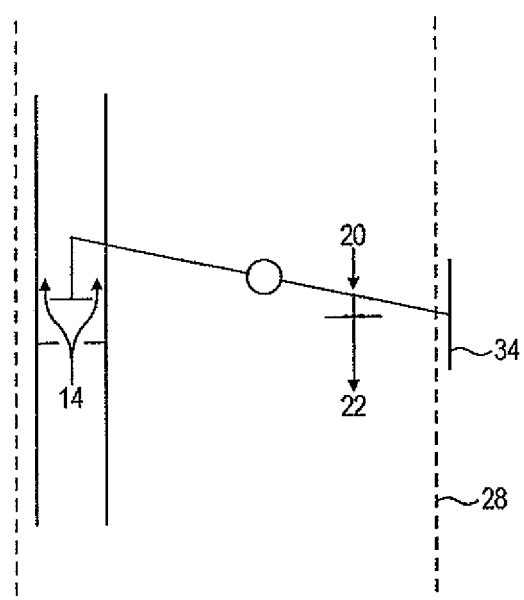

In one arrangement shown in FIGS. 5 and 6, the integrated control 30, 68 may comprise a mechanical linkage, such that operation of user input device 34 causes movement of a valve plate in valve 32 and connection of electrical contacts in switch 70. In more detail, the input device, or slide switch 34, is connected by a pivot arm to valve plate 74 and to electrical contact 76. In the condition of the mechanical linkage shown in FIG. 5, the valve plate 74 seals against a valve seat 78 closing gas flow. The electrical contact 76 is spaced from second electrical contact 80. In the condition shown in FIG. 6, the valve plate 74 is spaced from valve seat 78 opening gas flow and electrical contact between contact 76 and contact 80 is closed allowing the source of electrical energy 20 to energise the plasma generation means 22.

The source 20 of electrical energy may be one or more batteries and preferably the batteries are rechargeable. In this case, the housing 28 may comprise an electrical socket for receiving a plug connected to a mains power source and a recharging circuit 82 for recharging the batteries. Alternatively, the device comprises means for example primary windings in a recharging unit and secondary windings in the device connected to the batteries for inductively coupling the batteries to a recharging unit for recharging.

The handpiece 28 comprises an enclosure 84 for locating the batteries in the housing and electrical terminals (not shown) which connect to the batteries when they are located in the enclosure for supplying energy to the plasma energising means 22.

In order to permit a free range of movement of the device by a user, it is preferable that the source of electrical energy is not connected to a mains or other supply during use. It will also be appreciated that as the device may be used in a wet environment for instance a bathroom it is advantageous to avoid cabling. Further, some bathrooms do not have an electrical socket. However, the device 10 may be connected by an electrical cable to a socket during use. In this case, the source 20 of electrical energy may comprise a transformer and the housing comprises a socket for receiving a plug connected to an electrical power supply. The transformer is adapted to supply energy in a form suitable for the plasma energising means 22. The plug and transformer may be adapted for connection to the energy supply of a vehicle, for example by inserting the plug into a socket of a cigarette lighter of the vehicle and delivering suitable power to the plasma energising means.

The applicator 18 takes the form of a needle member for directing gas and plasma from the plasma generator 16 to an interdental (between teeth) region of the user's mouth. As shown schematically in FIG. 1, the applicator 18 comprises an outlet port 26 for forming the plasma plume or jet 24 and a duct 88 for ducting gas or plasma from the plasma generator 18 to the outlet port 26. The duct is preferably less than 1 mm in diameter which is sufficiently small to cause a rapid through flow of plasma to the treatment region. A velocity in the range of 20 m/s to 100 m/s is typically suitable for interdental use. The duct can be straight as shown but is preferably curvilinear to allow greater access to a treatment region of the user's mouth. The applicator has a length which is typically less than about 10 cm.

The outlet port 26 is spaced from the plasma generator sufficiently to protect a user from the high voltages used to generate the plasma and reduce the risk of contamination of the plasma chamber.

Two examples of interdental applicators are now described with reference to FIGS. 7 to 9.

Figure 7:
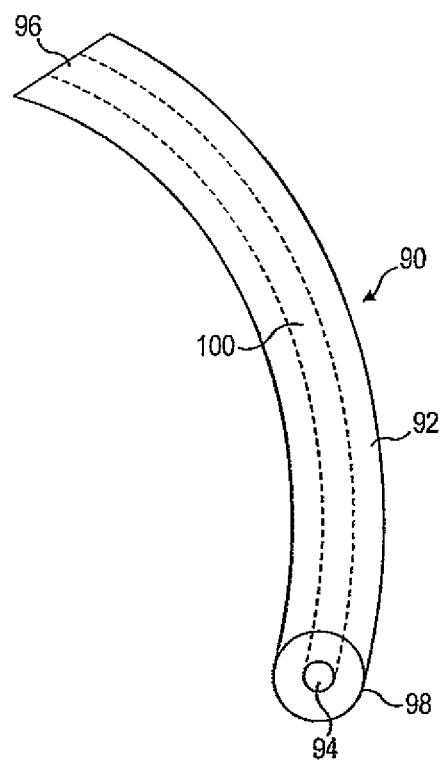
FIG. 7 shows a first applicator of the device.

Referring first to FIG. 7, an applicator 90 comprises a curvilinear hollow needle member 92, which is open at both its proximal end and its distal end so as to provide an inlet port 94 and an outlet port 96. The proximal end of the needle member 92 is typically bonded to or locked in an adaptor 98, the function and configuration of which will be described below. The bore of the needle member 92 forms a curvilinear passage 100.

The degree of curvature of the needle member 92 is such that if the device is held vertically, the outlet port directs the plasma jet towards 10 o'clock. This arrangement facilitates interdental cleaning of the user's front teeth.

The needle member 92 may be from 5 to 10 cm in length. The passage 100 preferably tapers from its proximal end of its distal end. The diameter of the inlet port 94 may typically be in the range 2-4 mm and the diameter of the outlet port 96 may typically be in the range 0.5-1 mm. The tapering of the passage 100 and the differential in diameter between the inlet port 94 and the outlet port 96 facilitate the creation of a high velocity (20 m/s-100 m/s) plasma jet suitable for interdental tooth cleaning. A high velocity jet is able better to penetrate the spaces between the user's teeth than a low velocity one. The user may simply hold the device according to the invention fitted with the applicator 90 close to his or her own teeth and direct the plasma at each gap in turn. The curvature of the needle member 92 enables the user to insert the applicator 90 into his or her own mouth and direct the plasma jet at the back of the teeth.

The gas from which the non-thermal plasma is formed is typically helium. Helium has two particular advantages. First, its ionisation energy is such that a non-thermal plasma can be formed in it with lower energy expenditure than most other gases. As a result, formation of a non-thermal plasma which feels neither too hot nor cold to the user is facilitated. Second, helium has a small atomic size and can therefore readily penetrate even tight inderdental spaces. The helium ions in the plasma readily react with oxygen and water vapour molecules to present in the interdental spaces to form singlet oxygen atoms and hydroxyl free radicals which are effective anti-bacterial agents. A non-thermal helium plasma is therefore able to destroy bacteria prevent in interdental spaces.

The needle member 92 may be essentially rigid or may be formed of a material that allows it to have some flexibility. The needle member 92 may, for example, be formed of plastics material or a metal alloy. Another alternative is to form the needle member with an outer sheath or sleeve (not shown). For example the needle member 92 may be formed of stainless steel and provided with a close fitting sheath of polyurethane or polythene, the fit being such that the sheath cannot readily be prised from the stainless steel member.

Figure 8:
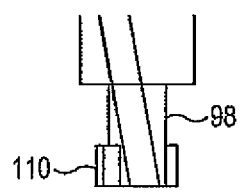
FIG. 8 illustrates the correction of the applicator shown in FIG. 7 to the handpiece of the device.
Figure 8:
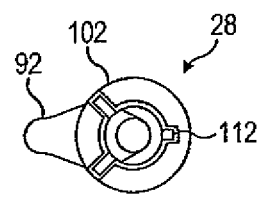

The adaptor 98 is shown in more detail in FIG. 8.

The adaptor 98 is configured to engage with a complementary connecting portion 102 at an end of the handpiece 28 for fixing the applicator 90 to the handpiece 28. The adaptor 98 comprises a plurality of formations, or keys, 110 which are received in a respective plurality of recesses, or key holes, 112 in the connecting portion 102. Once received in the recesses, the applicator and handpiece are relatively rotated to lock the applicator in place.

The adaptor 98 and connecting portion 102 are configured to allow activation of one or more functions of the device 10 when connected and to prevent activation of functions when not connected. Similarly, the connection of one applicator to the housing may allow activation of one set of functions whilst the connection of another applicator to the handpiece may activate another set of functions. The connection of applicator 90 to the handpiece 28 is, referring again to FIG. 1, configured to allow activation of the plasma energising means 22 and of gas flow to plasma chamber 16 when user input device 34 is operated. Without such connection, operation of the user input device cannot activate these functions.

Figure 10:
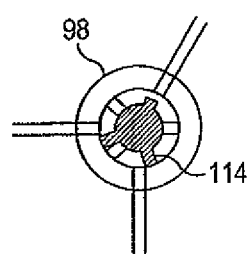
FIG. 10 shows schematically connection of the applicator shown in FIG. 7 to the handpiece.
Figure 10:
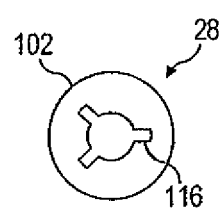

As schematically shown in FIG. 10, the adaptor 98 and the connection portion 102 may comprise complementary electrical contacts which are closed to allow activation of certain, selected, functions. The adaptor 98 is rotatable in connecting portion 102 to lock the applicator to the handpiece. When locked, electrical contacts 114 on the adaptor 98 contact electrical contacts 116 on the connecting portion 102 thereby closing respective electronic switches allowing activation of the gas flow by valve 32 and, activation of the plasma energising means by switch 70.

When a different applicator is connected to the housing different functions of the device are allowed. Different applicators may be adapted or configured to perform specific oral care functions. For example, the applicator 120 shown in FIG. 9, although generally, similar to the one shown in FIG. 7, is configured to be suitable for insertion by the user into his or her mouth to provide interdental treatment of the back teeth (when the applicator 120 is connected to the handpiece 28).

Figure 9:
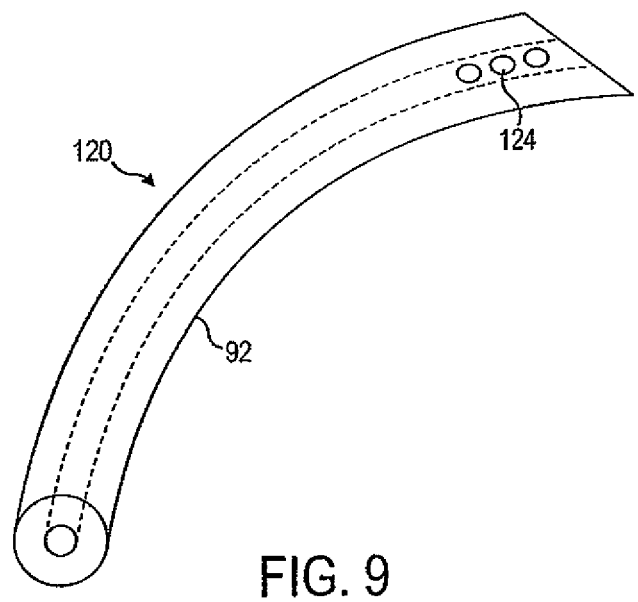
FIG. 9 shows a second applicator of the device.

The needle member 92 of the applicator shown in FIG. 9, therefore has a greater degree of curvature than the corresponding needle member 92 of the applicator 90 shown in FIG. 7. The other main difference is that the applicator 120 is closed at its distal end, but has three side ports 124 through the side of the needle member 92 at positions close to its distal end or tip. This arrangement is intended to facilitate interdental clearing of the back teeth.

The user may accordingly be provided with a kit comprising a single handpiece 28 and a set of interchangeable applicators, each adapted or configured to perform a different oral care function.

Referring again to FIG. 1, the device 10 may comprise a display 130 for displaying a value representative of a condition of the device, for example, one or more of the gas content of the gas capsule 12, the amount of charge remaining in the source of electrical energy 20, or a temperature of the plasma plume emitted from the applicator. The display may be a graphical LCD. Additionally or alternatively, means 132 may be provided for alerting a user when a condition of the device, such as gas content of the pressure vessel, charge in the source of electrical energy, or temperature of the plasma plume decreases or increases beyond a predetermined amount. The alerting means 132 may comprise means for generating a sound which is audible to user or a warning light, such as an LED, prompting the user to recharge or replace the gas capsule or the source or to remove the device from the treatment region to avoid harm.

Figure 11:
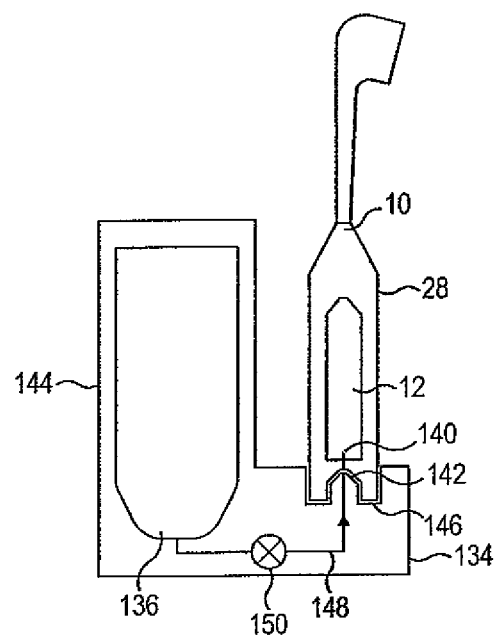
FIG. 11 shows the device seated in the charging unit from the other side.
Figure 12:
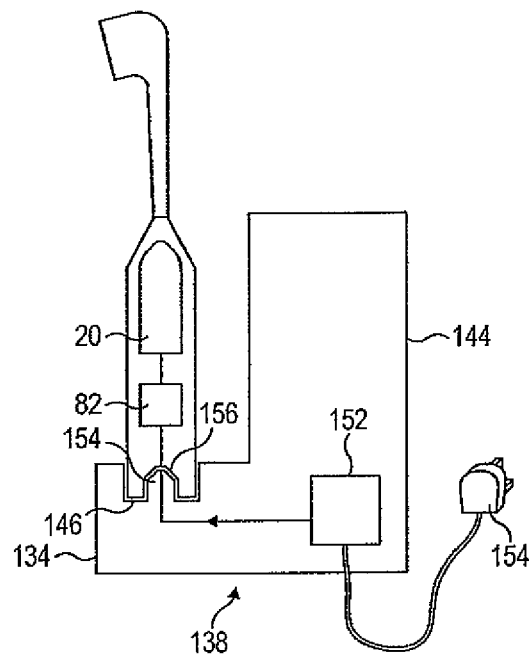
FIG. 12 shows the device seated in the recharging unit from one side.

Referring to FIGS. 11 and 12, apparatus is shown comprising device 10 and a recharging unit 134. The recharging unit comprises a recharging pressure vessel 136 containing gas for supplying gas to the gas capsule 12 of the device 10; and electrical recharging means 138 for recharging the source of electrical energy 20 in the device. In an alternative arrangement the recharging unit may comprise only one of the recharging pressure vessel 136 and the electrical recharging means 138. Replacement pressure vessels 12 may be used when a previous vessel is depleted of gas by use in the device, or fresh batteries are used to replace the source 20 when discharged.

The recharging unit and device gas capsule 12 comprise respective recharging valves 140, 142 which can be opened when the gas capsule are connected as shown to allow the supply of gas to the device gas capsule 12 and are closed when the pressure vessels are not connected. The valve arrangement may be similar to the arrangement shown in FIG. 3.

The recharging unit 134 consists of a stand having upright portion 144 for storing the recharging pressure vessel 136. The recharging pressure vessel is relatively larger and may have a larger volume of pressure and can contain sufficient gas to refill the device a multiplicity of times, perhaps as much as twenty times. The recharging unit also comprises a seat 146 for seating the device. When the device 10 is seated in the recharging unit the pressure vessels 12, 136 are connected to allow the supply of gas to the device gas capsule 12. In this regard, a conduit 148, optionally including a valve 150, is provided having a first end portion adapted for engaging with and opening the recharging valve 140 of the device gas capsule 12 and a second end portion connected to the recharging pressure vessel 136. Accordingly, when the device 10 is seated in the recharging unit 134, the pressure vessel 12 of the device 10 is automatically refilled.

In an alternative arrangement, rather than seating the whole of the device 10 on the recharging unit for recharging, the seat 146 seats a device gas capsule 12 when it has been removed from the device. Accordingly, when the device gas capsule 12 is seated in the recharging unit the pressure vessels 12, 136 are connected to allow the supply of gas to the device gas capsule.

In this case, the apparatus may comprise at least two device gas capsule 12. At any one time one or more device gas capsule 12 can be seated in the recharging unit 134 for recharging and one device gas capsule 12 can be housed in the device housing 28 for use in generating a gas flow.

As shown in FIG. 12, the electrical recharging means 138 comprises a control circuit 152 for receiving electrical energy from, for instance, a mains supply through a plug 154 and supplying the electrical energy for recharging the source of electrical energy 20 in the device 10 when the source of energy 20 is connected to the electrical recharging means 138. When the device is seated in the recharging unit in seat 146 the source of energy 20 is automatically connected to the electrical recharging means if the recharging unit is connected to the mains supply.

One of the seat 146 and the device 10 may include a formation, or protrusion, 154 and the other includes a recess 156 for mating for example for allowing close proximity of primary and secondary coils of an inductively coupled charging means for charging the source 20.

In an alternative arrangement, the source 20 may be recharged by removing it from the device 10 placing it on the seat 146 so that it is connected to the recharging unit and recharging it with the recharging means 138.

Figure 13:
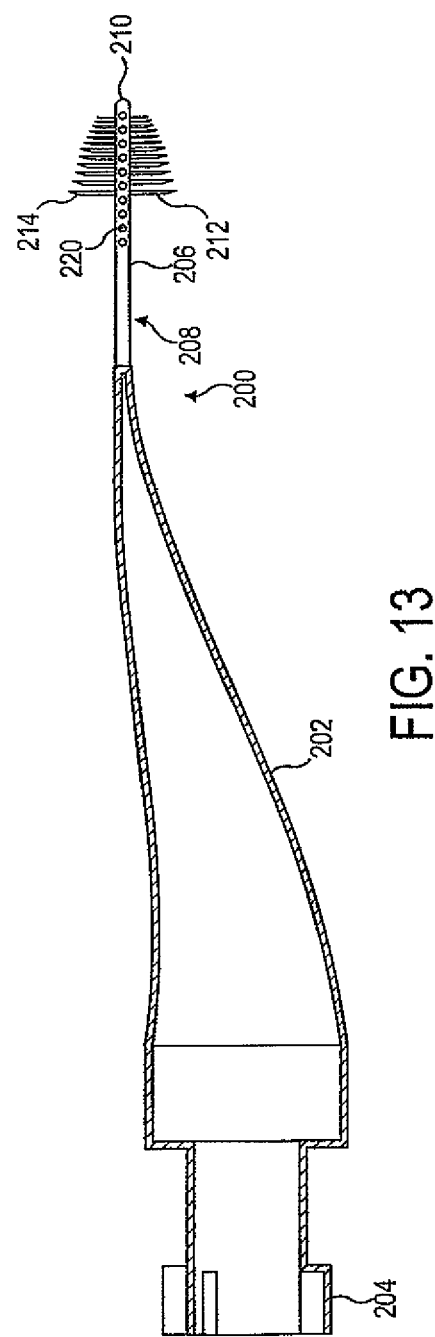
FIG. 13 shows a third applicator of the device.

Referring now to FIG. 13, there is shown a third applicator for use in a device according to the invention. The applicator, which is indicated by the reference numeral 200 in FIG. 13, comprises a hollow brush holder 202. The brush holder 202 has an adaptor 204 at its proximal end which enables the brush holder 202 to be connected to a handpiece (not shown in FIG. 13). The adaptor 204 is similar to the adaptor 98 described with reference to FIG. 10. The distal end of the brush holder 202 releasably engages on interdental brush 206. The brush 206 comprises a hollow, deformable, length of hollow wire 208 which at its head or distal end 210 is provided with an array of radially or laterally extending arms 212 each holding an array of bristles 214. The dimensions of the brush 206 are such that it can be inserted by a person between his or her teeth. The wire 208 is deformable such that if the brush 206 becomes stuck between the user's teeth, the wire 208 will absorb any force applied to free the brush 206 and the user's teeth will not be damaged. The brush 206 has a conventional cleaning effect if it is moved backwards and forwards in an interdental space. In accordance with the invention, this cleaning effect is enhanced by the supply of non-thermal gaseous plasma from the handpiece (not shown) through the brush holder 202 to the brush 206 itself. The head of the brush 206 is formed with a plurality of orifices. 220 for the discharge of the plasma. The orifices 220 may be formed in the wire 208. The non-thermal gaseous plasma may, as previously described, typically be formed of helium. The helium plasma mediates the formation of reactive anti-bacterial species such as oxygen and hydroxyl radicals. These radicals can destroy or damage the cells of any harmful oral bacterial present in the interdental spaces between teeth.

The brush 206 typically makes a push fit with the brush holder 202. The brush 206 may have a short operating life as repeated interdental insertions may seriously deform it. Accordingly, the device according to the invention may be supplied with a set of brushes 206.

The invention claimed is:

1. An interdental treatment device comprising a generator for creating a non-thermal gaseous plasma at a temperature suitable for use in oral treatment; an applicator of the non-thermal gaseous plasma, wherein the applicator comprises (i) a hollow needle member for directing a jet of the non-thermal plasma interdentally, the needle member having at least one inlet port and at least one outlet port, or (ii) an interdental brush having a hollow head for receiving the non-thermal gaseous plasma, the head having at least one lateral opening for the discharge of the non-thermal gaseous plasma; and a handpiece engageable with the applicator, wherein the handpiece houses the plasma generator and a gas capsule for storing a gas under pressure and for supplying a flow of gas to the plasma generator; wherein there is a conduit extending between the gas capsule and a plasma generator, the conduit having disposed therein a flow valve or flow regulator.

2. An interdental treatment device comprising a generator for creating a non-thermal gaseous plasma at a temperature suitable for use in oral treatment; an applicator of the non-thermal gaseous plasma, wherein the applicator comprises (i) a hollow needle member for directing a jet of the non-thermal plasma interdentally, the needle member having at least one inlet port and at least one outlet port, or (ii) an interdental brush having a hollow head for receiving the non-thermal gaseous plasma, the head having at least one lateral opening for the discharge of the non-thermal gaseous plasma; and a handpiece engageable with the applicator, wherein the handpiece houses the plasma generator and a gas capsule for storing a gas under pressure and for supplying a flow of gas to the plasma generator; and including an expansion chamber intermediate the gas capsule and the plasma generator.

3. An interdental treatment device comprising a generator for creating a non-thermal gaseous plasma at a temperature suitable for use in oral treatment; an applicator of the non-thermal gaseous plasma, wherein the applicator comprises (i) a hollow needle member for directing a jet of the non-thermal plasma interdentally, the needle member having at least one inlet port and at least one outlet port, or (ii) an interdental brush having a hollow head for receiving the non-thermal gaseous plasma, the head having at least one lateral opening for the discharge of the non-thermal gaseous plasma; and a handpiece engageable with the applicator, wherein the handpiece houses the plasma generator; and wherein the handpiece additionally houses a source of electrical energy and energising means electronically connected to the source of electrical energy for energising gas in the plasma generator to form said non-thermal gaseous plasma.

4. An interdental treatment device according to claim 3, wherein the energising means comprises at least one electrode for generating an electric field in said plasma generator and a signal generator for generating an electric signal for driving said electrode.

5. An interdental treatment device according to claim 4, wherein the said electrode is insulated by a dielectric from gas in the plasma generator.

6. An interdental treatment device according to claim 3, wherein the source of electrical energy is one or more disposable or rechargeable batteries.

* * * * *